United States Patent [19]
Kuhnt et al.

[11] Patent Number: 5,283,363
[45] Date of Patent: Feb. 1, 1994

[54] PROCESS FOR THE PREPARATION OF (HETERO)ARYLALK(EN/IN)YLAMINES AND (HETERO)ARYLALKINYLAMINES

[75] Inventors: Dietmar Kuhnt, Leverkusen; Thomas Himmler, Cologne; Heinz Ziemann, Leichlingen, all of Fed. Rep. of Germany

[73] Assignee: Bayer Aktiengesellschaft, Leverkusen, Fed. Rep. of Germany

[21] Appl. No.: 821,202

[22] Filed: Jan. 16, 1992

[30] Foreign Application Priority Data

Jan. 26, 1991 [DE] Fed. Rep. of Germany ....... 4102289

[51] Int. Cl.$^5$ ................. C07C 211/08; C07D 251/14; C07D 211/00
[52] U.S. Cl. ................................... 564/336; 544/180; 544/194; 544/218; 544/219; 544/220; 544/298; 544/322; 544/334; 546/286; 546/290; 546/304; 546/314; 548/127; 548/128; 548/129; 548/131; 548/132; 548/206; 548/213; 548/240; 549/29; 549/61; 549/62; 549/68; 564/374; 564/409; 564/383
[58] Field of Search ............... 564/336, 409, 412, 374, 564/383; 544/180, 194, 218, 219, 220, 298, 322, 334; 546/286, 290, 304, 314, 345; 548/127, 128, 129, 131, 132, 206, 213, 240, 243, 245; 549/29, 61, 62, 68, 429, 474, 475, 480, 484

[56] References Cited

U.S. PATENT DOCUMENTS 3,332,988  7/1967  Mull ................................ 562/114
4,743,617  5/1988  Bargar et al. .................... 514/438

FOREIGN PATENT DOCUMENTS 0030922  6/1981  European Pat. Off. .
0251786  1/1988  European Pat. Off. .
0252683  1/1988  European Pat. Off. .
8810264 12/1988  PCT Int'l Appl. .

OTHER PUBLICATIONS

Journal of Organic Chemistry, vol. 54, No. 14, (1989), Washington, D.C., pp. 3420-3422; Hobbs, Frank W., Jr.: "Palladium-Catalyzed Synthesis of Alkynylamino Nucleosides, A Universal Linker for Nucleic Acids".

J. Org. Chem., 51(12), 2191-202, (1986), Trybulski, E. J.; Fryer, R. I.; Reeder E.; Vitone, S.; Todaro, L.: "2-Benzazepines, 9 Synthesis and Chemistry of 3H-2--Benzazepine and Pyrimido[4,5-d][2]benzazepine Derivatives", p. 2191.

J. Org. Chem., 41(24), 3813-19, (1976), pp. 3813-3919; Klemm, LeRoy H.; Hwang, Yoon Ni, McGuire, Thomas M.: "Intramolecular Diels-Alder Reactions, 12, Competitive [4+2] and [2+2] Cycloadditions of N-(Phenylpropargyl)-cis-cinnamamide", p. 3818, Example 10.

Tetrahedron Lett., 23(43), 4517-20, (1982), Catellani, Marta; Chiusol, Gian Paolo: "One-Pot Palladium-Catalyzed Synthesis of 2,3-Disubstituted Bicyclo[2.2.1-]Heptanes and Bicyclo[2.2.1]hept-5-enes", p. 4519, lines 1-4.

Agents Actions, 17(2), 138-44, (1985), Banning, Jon W.; Griffith, Robert K.; Dipietro, Richard A.: "Histamine Receptor Activation by Unsaturated (Allyl and Propargyl) Homoglogs of Histamine", p. 138, FIG. I.

J. Med. Chem., 13(6), 1249-50, (1970), Simon, David Z.; Salvador, Romano L.; Champagne, Gaston: "Acetylenics. 1. Aromatic Amines Containing the Acetylenic Triple Bond".

Houben Weyl XI, 1 (1957) 68 ff.

F. C. Whitmore et al., Am. Chem. Soc. 67, 393 (1945).

Chemical Abstracts, 1082744 (1953).

Primary Examiner—Mukund J. Shah
Assistant Examiner—Y. N. Gupta
Attorney, Agent, or Firm—Sprung Horn Kramer & Woods

[57] ABSTRACT

The invention relates to a new process for the preparation of (hetero)arylalk(en/in)ylamines of the formula (I)

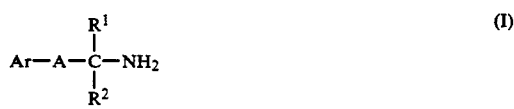

in which (Abstract continued on next page.)

ABSTRACT
— continued

A represents ethane-1,2-diyl (ethylene, dimethylene, —CH$_2$—CH$_2$—) or represents ethene-1,2-diyl (ethenylene, vinylene, —CH═CH—) or represents ethine-1,2-diyl (ethinylene, —C≡C—), characterized in that (a) in the event that, in formula (I), A represents ethine-1,2-diyl, halogeno(hetero)aryl compounds of the general formula (II)

$$Ar-X \qquad (II)$$

are reacted with aminoalkinyl compounds of the general formula (III)

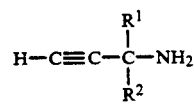

(III)

and, if appropriate, (b) in the event that, in formula (I), A represents ethane-1,2-diyl or ethene-1,2-diyl, the new (hetero)aralkinylamines which are obtained by the process step described under (a), of the general formula (Ia),

(Ia)

are reacted with a hydrogenating agent, if appropriate in the presence of a catalyst and if appropriate in the presence of a diluent, the definitions applying to Ar, R$^1$, R$^2$ and X being those mentioned in the description, and their use as intermediates for medicaments and plant protection agents, in this case in particular herbicides.

7 Claims, No Drawings

PROCESS FOR THE PREPARATION OF (HETERO)ARYLALK(EN/IN)YLAMINES AND (HETERO)ARYLALKINYLAMINES

The invention relates to a new process for the preparation of (hetero)arylalk(en/in)ylamines and to new (hetero) arylalkinylamines which can be used as intermediates for medicaments and plant protection agents, in this case in particular herbicides.

It is known that certain arylalkinylamines such as, for example, N-ethyl-1,1-dimethyl-3-phenyl-2-propinylamine, are obtained when suitable halogen compounds such as, for example, 1-chloro-1,1-dimethyl-3-phenyl-2-propine, are reacted with amino compounds such as, for example, ethylamine (cf. J. Org. Chem. 31 (1966), 122–127, in particular p. 123). However, the yield in this reaction is very low.

It is furthermore known that certain hydroxyalkinylaryl compounds such as, for example, N-[3-chloro-4-(3'-methyl-3'-hydroxybut-1'-in-1'-yl)-phenyl]-N'-methoxy-N'-methylurea, are obtained when suitable halogenoaryl compounds such as, for example, N-(3'-chloro-4'-bromophenyl)-N'-methoxy-N'-methylurea, are reacted with hydroxyalkinyl compounds such as, for example, 3-hydroxy-3-methyl-1-butine (cf. EP-A 30,922, in particular p. 9). However, an analogous reaction for the preparation of aminoalkinylaryl compounds was hitherto not known.

The present application relates to a new process for the preparation of (hetero)arylalk(en/in)ylamines of the general formula (I)

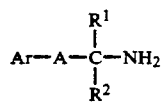

in which

A represents ethane-1,2-diyl (ethylene, dimethylene, —CH$_2$—CH$_2$—) or represents ethene-1, 2-diyl (ethenylene, vinylene, —CH=CH—) or represents ethine-1,2-diyl (ethinylene, —C≡C—), Ar represents in each case optionally substituted aryl or heteroaryl, and R$^1$ and R$^2$ are identical or different and individually represent hydrogen or alkyl or together represent alkanediyl (alkylene), characterised in that (a) in the event that, in formula (I), A represents ethine-1,2-diyl and Ar, R$^1$ and R$^2$ have the above-mentioned meaning, halogeno(hetero)aryl compounds of the general formula (II)

Ar—X (II)

in which

Ar has the abovementioned meaning and

X represents halogen, are reacted with aminoalkinyl compounds of the general formula (III)

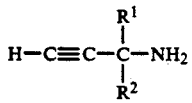

in which

R$^1$ and R$^2$ have the abovementioned meaning, in the presence of a catalyst, in the presence of an acid acceptor, if appropriate in the presence of further reaction auxiliaries and if appropriate in the presence of a diluent, at temperatures between 0° C. and 200° C., and, if appropriate, (b) in the event that, in formula (I), A represents ethane-1,2-diyl or ethene-1,2-diyl and Ar, R$^1$ and R$^2$ have the abovementioned meaning, the compounds obtained by the process step described under (a), of the general formula (Ia)

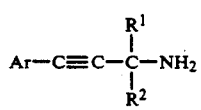

in which

Ar, R$^1$ and R$^2$ have the abovementioned meaning, are reacted with a hydrogenating agent, if appropriate in the presence of a catalyst and if appropriate in the presence of a diluent, at temperatures between 0° C. and 150° C.

Surprisingly, the (hetero)arylalkinylamines of the formula (Ia) can be prepared in a simple manner in high yields and in very good quality using process step (a) in the process according to the invention. The nucleophilic attack of the amino group of the compounds of the formula (III) on the halogenated position of the halogeno(hetero)aryl compounds of the formula (II), which was to be expected as a side reaction, is not apparent to a substantial extent.

The process according to the invention—both as process step (a) on its own as well as in the combination of process steps (a) and (b)—is therefore a valuable addition to the prior art.

The compounds which are to be prepared by the process step described above under (a), of the formula (Ia)

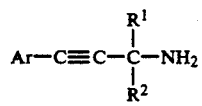

in which

Ar represents in each case optionally substituted aryl or heteroaryl and

R$^1$ and R$^2$ are identical or different and individually represent halogen or alkyl or together represent alkanediyl (alkylene), are new with the exception of 3-phenyl-2-propinylamine and 1-methyl-3-phenyl-2-propinylamine (both known from J. Med. Chem. 13 (1970), 1249–1250) as well as N'-[3-(3-amino-3-methyl-1-butinyl)-phenyl]-N-methoxy-N-methyl-urea (known from EP-A 30,922, Example 2.70, p. 19) and, as new substances, are a subject of the present invention.

These new (hetero)arylalkinylamines of the formula (Ia) can be used as intermediates for the preparation of medicaments and plant protection agents.

Compounds of the formula (I) which are preferably prepared by the process according to the invention are those in which A represents ethane-1,2-diyl (ethylene, dimethylene, —CH$_2$—CH$_2$—) or represents ethene-1, 2-diyl (ethenylene, vinylene, —CH=CH—) or represents ethine-1,2-diyl (ethinylene, —C≡C—), Ar represents in each case optionally substituted aryl or heteroaryl, each of which has up to 10 carbon atoms and where appropriate 1 to 3 nitrogen atoms and/or one oxygen or sulphur atom as hetero atom(s), the following being selected as preferred substituents:

halogen, cyano, nitro, in each case straight-chain or branched alkyl, alkoxy, alkylthio or dialkylamino, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 8 carbon atoms in the individual alkyl moieties, cycloalkyl having 3 to 7 carbon atoms, divalent alkanediyl having 3 to 5 carbon atoms, or alkylenedioxy which has 1 or 2 carbon atoms and which is optionally monosubstituted to tetrasubstituted by fluorine and/or chlorine, or aryl, aralkyl, aryloxy, aryloxyalkyl or aralkoxy, each of which has 6 to 10 carbon atoms in the aryl moiety and where appropriate 1 to 4 carbon atoms in the straight-chain or branched alkyl moiety and each of which is optionally monosubstituted or polysubstituted in the aryl moiety by identical or different substituents from the series comprising halogen, alkyl, alkoxy, alkylthio, halogenoalkyl, halogenoalkoxy or halogenoalkylthio, each of which has 1 to 4 carbon atoms and where appropriate 1 to 9 identical or different halogen atoms, or represents heteroarylalkyl or heteroaryl, each of which has 2 to 9 carbon atoms and 1 to 4 identical or different hetero atoms—in particular nitrogen, oxygen and/or sulphur in the heteroaryl moiety and where appropriate 1 to 4 carbon atoms in the straight-chain or branched alkyl moiety and each of which is optionally monosubstituted or polysubstituted in the heteroaryl moiety by identical or different substituents from the series comprising halogen, alkyl, alkoxy, alkylthio, halogenoalkyl, halogenoalkoxy or halogenoalkylthio, each of which has 1 to 4 carbon atoms and where appropriate 1 to 9 identical or different halogen atoms; and R$^1$ and R$^2$ are identical or different and individually represent hydrogen or straight-chain or branched alkyl having 1 to 6 carbon atoms, or together represent alkanediyl (alkylene) having 2 to 6 carbon atoms.

In particular, compounds of the formula (I) which are prepared by the process according to the invention are those in which A represents ethane-1,2-diyl (ethylene, dimethylene, —CH$_2$—CH$_2$—) or represents ethene-1,2-diyl (ethenylene, vinylene, —CH=CH—) or represents ethine-1,2-diyl (ethinylene, —C≡C—), Ar represents phenyl, naphthyl, pyridyl, pyrimidyl, triazinyl, furyl, (iso)oxazolyl, oxadiazolyl, thienyl, (iso)thiazolyl or thiadiazolyl, each of which is optionally monosubstituted to trisubstituted, the following being selected as particularly preferred substituents:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, dimethylamino, difluoromethyl, trifluoromethyl, difluoromethoxy, trifluoromethoxy, difluoromethylthio, trifluoromethylthio, methoxycarbonyl, ethoxycarbonyl, n- or i-propoxycarbonyl, methoximinomethyl, ethoximinomethyl, methoximinoethyl, ethoximinoethyl, cyclohexyl, or represents phenyl, benzyl, phenoxy, phenoxymethyl or benzyloxy, each of which is optionally monosubstituted to trisubstituted in the phenyl moiety by identical or different substituents selected from the series comprising fluorine, chlorine, bromine, methyl, ethyl, methoxy, ethoxy, methylthio, trifluoromethyl, difluoromethoxy, trifluoromethoxy and/or trifluoromethylthio, R$^1$ represents hydrogen, methyl, ethyl or n- or i-propyl, and R$^2$ represents methyl, ethyl, n- or i-propyl or n- or i-butyl, or together with R$^1$ represents ethane-1,2-diyl (dimethylene), propane-1,3-diyl (trimethylene), butane-1,4-diyl (tetramethylene) orpentane-1,5-diyl (pentamethylene).

Preferred or particularly preferred as new substances of the formula (Ia) are those compounds of the formula (Ia) in which Ar, R$^1$ and R$^2$ have those meanings which are given above in connection with the description of the compounds of the formula (I) to be prepared according to the invention as being preferred, or as particularly preferred, for Ar, R$^1$ and R$^2$, the known compounds 3-phenyl-2-propinylamine and 1-methyl-3-phenyl-2-propinylamine being excepted by disclaimers.

If, for example, bromobenzene and 3-amino-3-methyl-1-propine are used as the starting substances in the step of the process according to the invention described above under (a), and, subsequently, one or two mol equivalents of hydrogen are used as the hydrogenating agent in the process step described above under (b), the course of the reaction in the process according to the invention can be outlined by the following equation:

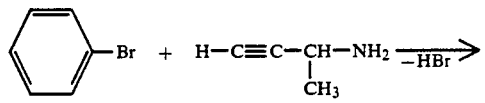

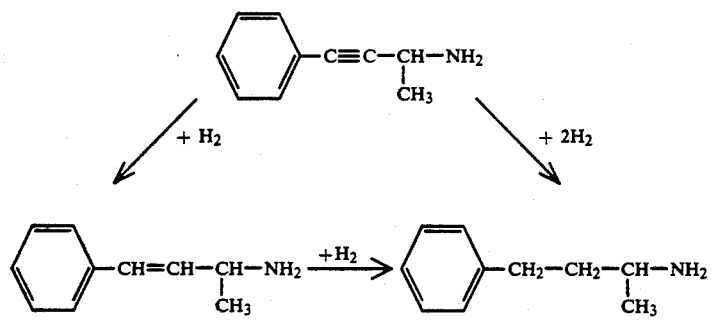

In the following text, the process step described above under (a) will be referred to as process (a) and the step described under (b) will be referred to as process (b).

Formula (II) provides a general definition of the halogeno(hetero)aryl compounds to be used as starting substances in process (a) according to the invention for the preparation of compounds of the formula (I).

In formula (II), Ar preferably, or in particular, has the meaning which has already been given above in connection with the description of the compounds of the formula (I) to be prepared according to the invention as being preferred, or as particularly preferred, for Ar; X preferably represents chlorine, bromine or iodine, in particular bromine or iodine.

Examples of the starting substances of the formula (II) which may be mentioned are: chloro-, bromo- and iodo-benzene, 3-fluoro-, 4-fluoro- and 3,4-difluorobromobenzene, 3-chloro- and 4-chlorobromobenzene, 3-bromo- and 4-bromo-benzonitrile, 3-bromo- and 4-bromo-toluene, 3-bromo- and 4-bromo-1-methoxybenzene, 3-bromo- and 4-bromo-benzotrifluoride, methyl 4-bromo-benzoate, 2-bromo-, 3-bromo- and 4-bromopyridine, 1-bromo- and 2-bromo-naphthalene, 2-bromo-, 4-bromo- and 5-bromo-pyrimidine, 2-bromo- and 3-bromo-furan, 2-bromo-, 4-bromo- and 5-bromo-oxazole, 2-bromo- and 3-bromo-thiophene, and 2-chloro-4,6-dimethylpyrimidine.

The starting substances of the formula (II) are known chemicals for organic synthesis.

Formula (III) provides a general definition of the aminoalkinyl compounds furthermore to be used as starting substances in process (a) according to the invention for the preparation of compounds of the formula (I).

In formula (III), $R^1$ and $R^2$ preferably, or in particular, have those meanings which have already been given above in connection with the description of the compounds of the formula (I) according to the invention as being preferred, or as particularly preferred, for $R^1$ and $R^2$.

The following may be mentioned as examples of the starting substances of the formula (III): 3-amino-3-methyl-1-propine, 3-amino-3-ethyl-1-propine, 3-amino-3,3-dimethyl-1-propine, 3-amino-3,3-diethyl-1-propine, 3-amino-3-methyl-3-ethyl-1-propine, 3-amino-3-methyl-3-propyl-1-propine and 1-amino-1-ethinyl-cyclohexane.

The starting substances of the formula (III) are known chemicals for organic synthesis.

Process (a) according to the invention is carried out in the presence of a catalyst. Catalysts which can preferably be used in this context are noble metals such as, for example, silver, gold, ruthenium, rhodium, palladium, osmium, iridium and platinum, in particular palladium and platinum, but also noble metal compounds such as, for example, palladium(II) acetate, palladium(II) acetylacetonate, palladium(II) bromide, palladium(II) chloride, palladium(II) iodide, palladium(II) oxide, palladium(II) sulphate, palladium(O)-tetrakis(triphenylphosphine), palladium(II)-bis(triphenylphosphine) dichloride, platinum(II) acetylacetonate, platinum(II)-bis(triethylphosphine) dichloride, platinum(II)-bis(triphenylphosphine) dichloride, platinum(II) bromide, platinum(II) chloride, platinum(II) iodide, platinum(IV) oxide and platinum(O)-tetrakis(triphenylphosphine). Acid acceptors which can be employed in process (a) according to the invention are all acid-binding agents which can customarily be used for reactions of this type. The following are preferably suitable: alkali metal hydrides and alkaline earth metal hydrides such as lithium hydride, sodium hydride, potassium hydride and calcium hydride, alkali metal hydroxides and alkaline earth metal hydroxides such as lithium hydroxide, sodium hydroxide, potassium hydroxide and calcium hydroxide, alkali metal carbonates, alkaline earth metal carbonates, alkali metal hydrogen carbonates and alkaline earth metal hydrogen carbonates such as sodium carbonate and potassium carbonate or sodium hydrogen carbonate and potassium hydrogen carbonate, and also calcium carbonate, alkali metal acetates such as sodium acetate and potassium acetate, alkali metal alcoholates such as sodium methylate, sodium ethylate, sodium propylate, sodium isopropylate, sodium butylate, sodium isobutylate, sodium tertbutylate, potassium methylate, potassium ethylate, potassium propylate, potassium isopropylate, potassium butylate, potassium isobutylate and potassium tertbutylate, furthermore basic nitrogen compounds such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo[5,4,0]-undec-7-ene (DBU) and 1,4-diazabicyclo-[2,2,2]-octane (DABCO).

If appropriate, process (a) according to the invention is carried out in the presence of further reaction auxiliaries. Suitable as such are mainly copper and/or copper compounds such as, for example, copper(I) chloride, copper(I) bromide, copper(I) iodide and copper(I) oxide, and, if appropriate, additionally also trialkyl- or triarylphosphines such as, for example, tributylphosphine or triphenylphosphine but also phase transfer catalysts such as, for example, benzyltributylammonium chloride, benzyltributylammonium bromide, benzyltriethylammonium chloride, butyltriphenylphosphonium chloride, ethyltrioctylphosphonium bromide, hexadecyltrimethylammonium bromide, methyltrioctylammonium chloride and tetrabutylammonium bromide.

Process (a) according to the invention is preferably carried out in the presence of a diluent. Suitable diluents in this context are virtually all inert organic solvents, but preferably aprotic polar solvents such as, for example, dibutyl ether, glycol dimethyl ether, diglycol dimethyl ether, tetrahydrofuran, dioxane, ethyl acetate, propyl acetate, isopropyl acetate, butyl acetate, isobutyl acetate and sec-butyl acetate, acetonitrile and propionitrile, dimethylformamide, dimethylacetamide, N-methyl-pyrrolidone, dimethyl sulphoxide and tetramethylene sulphone. In the event that basic nitrogen compounds are used as acid acceptors, they can also act as diluents when employed in excess.

When carrying out process (a) according to the invention, the reaction temperatures can be varied within a substantial range. In general, the process is carried out at temperatures between 0° C. and 200° C., preferably at temperatures between 20° C. and 150° C.

Process (a) according to the invention is generally carried out under atmospheric pressure. However, it is also possible to carry out the process under increased or reduced pressure, in general between 10 mbar and 10,000 mbar.

For carrying out process (a) according to the invention, between 0.5 and 1.5 mol, preferably between 0.9 and 1.3 mol, of an aminoalkinyl compound of the formula (III) and between 0.001 and 0.1 mol, preferably between 0.005 and 0.05 mol, of catalyst are generally employed per mol of halogeno(hetero)aryl compound of the formula (II).

For carrying out process (a), the reactants can be combined in any desired sequence.

In a preferred embodiment of process (a) according to the invention, the starting substances of the formulae (II) and (III) are mixed with the diluent, which is optionally identical to the acid acceptor, at temperatures between 0° C. and 50° C., preferably between 10° C. and 30° C. The catalyst and, if appropriate, one or more further reaction auxiliaries and, if appropriate, an acid acceptor, are then added, and the reaction mixture is then stirred at increased temperature between 50° C. and 200° C., preferably between 80° C. and 150° C., until the reaction is complete. Working-up can then be carried out by customary methods.

For example, the mixture is filtered, the filtrate is concentrated under reduced pressure, the residue is shaken with water and with an organic solvent which is virtually immiscible with water such as, for example, methylene chloride, and the organic phase is separated off, dried and filtered. The solvent is carefully removed from the filtrate by distillation under a water-pump vacuum. The crude product which remains can be purified further in the customary manner, for example by distillation in vacuo.

Process (b) according to the invention is carried out using a hydrogenating agent. Suitable agents for this purpose are those which are customary for the hydrogenation of alkines. These include, for example, sodium in liquid ammonia, sodium borohydride, sodium formate, cyclohexene, hydrazine, hydroxylamine and hydrogen. Process (b) is preferably carried out as a catalytic hydrogenation with hydrogen in the presence of a suitable catalyst.

Catalysts which are suitable for process (b) are the metals or metal compounds customarily used in catalytic hydrogenation. Insafar as the hydrogenation is intended to lead to saturated products (I, A=ethane-1,2-diyl), it is preferably carried out using Raney nickel, palladium or platinum, if appropriate on a suitable support material such as, for example, active carbon. If the hydrogenation is only intended to lead up to the alkene level (I, A=ethene-1,2-diyl), modified catalysts such as, for example, the so-called Lindlar catalyst (palladium on calcium carbonate, if appropriate doped with a lead compound such as, for example, lead(II) acetate), are preferably used (in connection with hydrogenating agents and catalysts, cf. Houben-Weyl, methoden der organischen Chemie [Methods in Organic Chemistry], 4th edition, Volume 5/2a (1977), p. 687–700, Georg-Thieme-Verlag, Stuttgart).

Process (b) is preferably carried out in the presence of a diluent. Diluents which are preferably used in process (b) are alcohols such as methanol, ethanol, propanol and isopropanol, ethers such as glycol dimethyl ether, diglycol dimethyl ether, tetrahydrofuran and dioxane, or esters such as methyl acetate, ethyl acetate, propyl acetate, isopropyl acetate, butyl acetate, isobutyl acetate and sec-butyl acetate.

When carrying out process (b) according to the invention, the reaction temperatures can be varied within a substantial range. In general, the process is carried out at temperatures between 0° C. and 150° C., preferably at temperatures between 10° C. and 80° C.

In general, process (b) is carried out under atmospheric pressure or increased pressure up to approximately 200 bar, preferably up to approximately 100 bar.

Process (b) is carried out under the reaction conditions which are customary in the case of hydrogenations. In a preferred embodiment of process (b), the intermediate of the formula (Ia) is mixed with a catalyst and a diluent, and the hydrogenating agent is metered into this mixture with stirring, until one or two mol equivalents thereof have been reacted.

Working-up can be carried out in the customary manner. For example, the mixture is filtered, the filtrate is concentrated under reduced pressure, and, if appropriate, the crude product which remains is purified further by distillation in vacuo.

The (hetero)arylalk(en/in)ylamines of the formula (I) to be prepared by the process according to the invention can be used as intermediates for medicoments and plant protection agents (cf. DE-OS (German Published Specification) 3,434,271, EP-A 294,666, Preparation Examples).

PREPARATION EXAMPLES

EXAMPLE 1

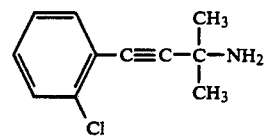

96.7 g (0.50 mol) of 1-bromo-2-chloro-benzene and 45.7 g (0.55 mol) of 3-amino-3,3-dimethyl-1-propine are introduced into 500 ml of triethylamine. After 7.0 g (0.01 mol) of palladium(II)-bis(triphenylphosphine) dichloride, 7.6 g (0.04 mol) of copper(I) iodide and 21.0 g (0.4 mol) of triphenylphosphine have been added, the reaction mixture is refluxed for 24 hours. It is then filtered and the filtrate is concentrated under a water-pump vacuum. The residue is extracted with methylene chloride/water (approx. 300 ml/300 ml), and the organic phase is separated off, dried with sodium sulphate and filtered. The solvent is removed from the filtrate by distillation under a water-pump vacuum, and the crude product which remains is purified by distillation under an oil-pump vacuum.

74.1 g (75 % of theory) of 3-amino-3,3-dimethyl-1-(2-chloro-phenyl)-1-propine of refractive index $n_D^{21}=1.5799$, of a boiling range of b.p. : 73°–75° C. at 0.1 mbar are obtained.

EXAMPLE 2

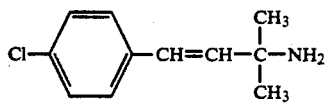

In a Parr hydrogenation apparatus, 96.8 g (0.50 mol) of 3-amino-3,3-dimethyl-1-(4-chloro-phenyl)-1-propine are mixed with 400 ml of tetrahydrofuran, and 13.0 g of Lindlar catalyst (5% of palladium on calcium carbonate, doped with lead) are added. The mixture is then shaken under a hydrogen pressure of 3 bar at a temperature which is gradually increased from 25° C. to 50° C. until the calculated hydrogen uptake is complete (1 mol equivalent after approximately 15 hours). The mixture is then filtered, the filtrate is concentrated under a water-pump vacuum, and the crude product which remains is purified by distillation in an oil-pump vacuum.

67.5 g (69 % of theory) of 3-amino-3,3-dimethyl-1-(4-chloro-phenyl)-1-propene of refractive index $n_D^{21}=1.5528$ are obtained.

EXAMPLE 3

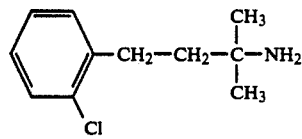

In a stirred autoclave, 40.6 g (0.21 mol) of 3-amino-3,3-dimethyl-1-(2-chloro-phenyl)-1-propine are mixed with 250 ml of tetrahydrofuran, and 10 g of Raney nickel are added. Hydrogen is then metered in up to a pressure of 50 bar, and the stirred mixture is gradually heated from 25° C. to 40° C. Every time the hydrogen pressure drops to 40 bar, it is readjusted to 50 bar, until the pressure remains constant. The mixture is subsequently filtered, the filtrate is concentrated under a water-pump vacuum, and the crude product which remains is distilled under an oil-pump vacuum.

31.8 g (77 % of theory) of 3-amino-3,3-dimethyl-1-(2-chloro-phenyl)-propane of refractive index $n_D^{21}=1.4817$ are obtained.

The compounds of the formula (I) listed in Table 1 below were also prepared analogously to Examples 1 to 3 and following the general description of the preparation process according to the invention.

TABLE 1

$$\text{Ar—A—}\underset{\underset{R^2}{|}}{\overset{\overset{R^1}{|}}{C}}\text{—NH}_2 \quad (I)$$

| Ex. No. | Ar | A | $R^1$ | $R^2$ | Physical data |
|---|---|---|---|---|---|
| 4 | 3-F₃C-phenyl | —C≡C— | CH₃ | CH₃ | b.p. 72° C.–74° C. (at 0.2 mbar) |
| 5 | 4-F₂CHO-phenyl | —C≡C— | CH₃ | CH₃ | b.p. 88° C.–90° C. (at 0.2 mbar) |
| 6 | 3-Cl-4-F₃C-phenyl | —C≡C— | CH₃ | CH₃ | b.p. 84° C.–86° C. (at 0.08 mbar) |
| 7 | 4-(CH₃)₃C-phenyl | —C≡C— | CH₃ | CH₃ | m.p. 57° C.–59° C. |
| 8 | 4-F₃CS-phenyl | —C≡C— | CH₃ | CH₃ | b.p. 72° C. (at 0.05 mbar) |

TABLE 1-continued $$Ar-A-\underset{\underset{R^2}{|}}{\overset{\overset{R^1}{|}}{C}}-NH_2 \quad (I)$$

| Ex. No. | Ar | A | $R^1$ | $R^2$ | Physical data |
|---|---|---|---|---|---|
| 9 | 4-F₃CO-C₆H₄- | —C≡C— | CH₃ | CH₃ | b.p. 75° C.–76° C. (at 1 mbar) |
| 10 | 4-Cl-2-CH₃-C₆H₃- | —C≡C— | CH₃ | CH₃ | b.p. 99° C.–102° C. (at 0.6 mbar) |
| 11 | 4-(CH₃)₂N-C₆H₄- | —C≡C— | CH₃ | CH₃ | m.p. 79° C.–81° C. |
| 12 | 4-H₃CO-C₆H₄- | —C≡C— | CH₃ | CH₃ | m.p. 44° C.–46° C. |
| 13 | 3-H₇C₃OOC-C₆H₄- | —C≡C— | CH₃ | CH₃ | b.p. 155° C. (at 2 mbar) |
| 14 | 2-H₇C₃OOC-C₆H₄- | —C≡C— | CH₃ | CH₃ | b.p. 149° C. (at 0.5 mbar) |
| 15 | C₆H₅- | —C≡C— | CH₃ | CH₃ | b.p. 73° C. (at 0.3 mbar) |
| 16 | C₆H₅- | —C≡C— | —(CH₂)₅— | | b.p. 123° C. (at 0.8 mbar) |
| 17 | 3-NC-C₆H₄- | —C≡C— | CH₃ | CH₃ | m.p. 63° C. |
| 18 | 3-H₅C₂OOC-C₆H₄- | —C≡C— | CH₃ | CH₃ | b.p. 128° C. (at 0.2 mbar) |
| 19 | 4-NC-C₆H₄- | —C≡C— | CH₃ | CH₃ | m.p. 84° C. |

TABLE 1-continued $$Ar-A-\underset{R^2}{\overset{R^1}{\underset{|}{C}}}-NH_2 \qquad (I)$$

| Ex. No. | Ar | A | R¹ | R² | Physical data |
|---|---|---|---|---|---|
| 20 | 4-Cl-C₆H₄- | -C≡C- | CH₃ | CH₃ | m.p. 32° C. |
| 21 | 4-(H₅C₂OOC)-C₆H₄- | -C≡C- | CH₃ | CH₃ | b.p. 145° C. (at 1 mbar) |
| 22 | 4-Cl-C₆H₄- | -C≡C- | C₂H₅ | C₂H₅ | b.p. 122° C. (at 0.5 mbar) |
| 23 | 3-pyridyl | -C≡C- | CH₃ | CH₃ | b.p. 75-78° C. (at 0.05 mbar) |
| 24 | 2,4-di-Cl-C₆H₃- | -C≡C- | CH₃ | CH₃ | b.p. 135-140° C. (at 0.5 mbar |
| 25 | 4-biphenyl | -C≡C- | CH₃ | CH₃ | m.p. 78-80° C. |
| 26 | 2,3-(OCF₂CF₂O)-C₆H₃- (4-yl) | -C≡C- | CH₃ | CH₃ | b.p. 88° C. (at 1-2 mbar) m.p. 42-44° C. |
| 27 | 4,6-dimethylpyrimidin-2-yl | -C≡C- | CH₃ | CH₃ | m.p. 63-64° C. |
| 28 | 2-pyridyl | -C≡C- | CH₃ | CH₃ | m.p. 70-73° C. |

EXAMPLE 29

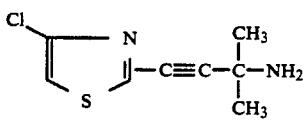

46.2 g (0.30 mol) of 2,4-dichloro-thiazole and 24.9 g (0.30 mol) of 3-amino-3, 3-dimethyl-1-propine are introduced into 300 ml of triethylamine. After 2.1 g (0.003 mol) of palladium(II)-bis(triphenylphosphine) dichloride, 2.28 g (0.012 mol) of copper(I) iodide and 3.2 g (0.012 mol) of triphenylphosphine have been added, the reaction mixture is refluxed for 19 hours. It is then filtered, the filtrate is concentrated under a water-pump vacuum, the residue is taken up in chloroform, and the mixture is extracted by shaking with dilute aqueous hydrochloric acid. The aqueous phase is rendered alkaline using sodium hydroxide solution and extracted several times by shaking with chloroform. After the organic phase has been dried over sodium sulphate, it is concentrated and the residue is chromatographed over silica gel (mobile phase: methylene chloride/methanol (96/4). 15.6 g (26 % of theory) of 3-amino-3, 3-dimethyl-1-(4-chloro-thiazol-2-yl)-1-propine with a melting point of 62–640° C. are obtained.

EXAMPLE 30

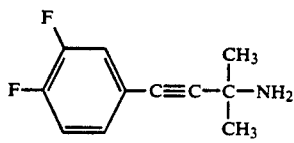

155 g (0.8 mol) of 3,4-difluoro-bromobenzene and 75 g (0.9 mol) of 3-amino-3, 3-dimethyl-1-propine are introduced into 900 ml of triethylamine. After 2.81 g (0.004 mol) of palladium(II)-bis(triphenylphosphine) dichloride, 3.05 g (0.016 mol) of copper(I) iodide and 8.4 g (0.032 mol) of triphenylphosphine have been added, the reaction mixture is refluxed for 4 hours. It is subsequently filtered, the filtrate is concentrated under a water-pump vacuum, and the residue is distilled under an oil-pump vacuum. 137 g (86% of theory) of 3-amino-3,3-dimethyl-1-(3,4-difluoro-phenyl)-1-propine of boiling point 75° C. at 1.5 mbar are obtained.

The compounds of the formula (I) which are listed below were also prepared analogously to Example 30.

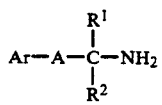

TABLE 1 (continuation)

| Ex. No. | Ar | A | $R^1$ | $R^2$ | Physical data |
|---|---|---|---|---|---|
| 31 | H$_3$C—⌬— | —C≡C— | CH$_3$ | CH$_3$ | b.p. 02° C. (at 1.5 mbar) |
| 32 | H$_5$C$_2$—⌬— | —C≡C— | CH$_3$ | CH$_3$ | b.p. 82–88° C. (at 0.8 mbar) |
| 33 | F$_3$C—⌬— | —C≡C— | CH$_3$ | CH$_3$ | b.p. 79° C. (at 1.5 mbar) m.p. 41–42° C. |
| 34 | HF$_2$C—⌬— | —C≡C— | CH$_3$ | CH$_3$ | m.p. 36–37° C. |
| 35 | ⌬S— | —C≡C— | CH$_3$ | CH$_3$ | b.p. 77–78° C. (at 0.6 mbar) |

EXAMPLE FOR USE AS INTERMEDIATES

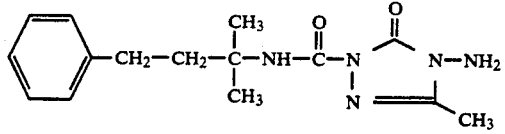

A mixture of 5.5 g (0.02 mol) of 4-isopropylideneimino-3-methyl-1-phenoxycarbonyl-1,2,4-triazolin-5-one (disclosed in EP-A 294,666, Example X-1, p. 48), 3.3 g (0.02 mol) of 3-amino-3,3-dimethyl-1-phenyl-propane and 100 ml of tetrahydrofuran is stirred for 18 hours at 20° C. and subsequently concentrated under a water-pump vacuum. To the residue which remains there are added 100 ml of ethanol, 20 ml of water and 10 ml of concentrated hydrochloric acid, and this mixture is stirred for 3 hours at 60° C./200 mbar and concentrated. The residue which remains in this process is taken up in 100 ml of methylene chloride, this solution is extracted with 50 ml of saturated aqueous sodium hydrogen carbonate solution and subsequently dried with magnesium sulphate and filtered. The filtrate is concentrated under a water-pump vacuum, the residue is brought to crystallisation by trituration with diethyl ether, and the crystalline product is isolated by filtering with suction.

3.64 g (60 % of theory) of 1-(1,1-dimethyl-3-phenyl-propyl-amino-carbonyl)-3-methyl-4-amino-1,2,4-triazolin-5-one of melting point 87° C. are obtained.

This compound is mentioned in EP-A 294,666 as Preparation Example (No. 132); it can be used as a herbicide.

It is understood that the specification and examples are illustrative but not limitative of the present invention and that other embodiments within the spirit and scope of the invention will suggest themselves to those skilled in the art.

What is claimed is:

1. A process for the preparation of (hetero) arylalk-(en/in)-ylamines of the general formula (I)

in which
   A represents ethane-1, 2-diyl (ethylene, dimethylene, —CH$_2$—CH$_2$—) or represents ethene-1,2-diyl (ethenylene, vinylene, —CH=CH—) or represents ethine-1,2-diyl (ethinylene, —C≡C—),
   Ar represents in each case optionally substituted aryl or heteroaryl, and
   R$^1$ and R$^2$ are identical or different and individually represent hydrogen or alkyl or together represent alkanediyl (alkylene),
characterised in that
   (a) in the event that, in formula (I), A represents ethine-1,2-diyl and Ar, R$^1$ and R$^2$ have the abovementioned meaning,
halogeno(hetero)aryl compounds of the general formula (II)

in which
   Ar has the abovementioned meaning and
   X represents halogen,
are reacted with aminoalkinyl compounds of the general formula (III)

in which
   R$^1$ and R$^2$ have the abovementioned meaning, in the presence of a catalyst, in the presence of an acid acceptor, if appropriate in the presence of further reaction auxiliaries and if appropriate in the presence of a diluent, at temperatures between 0° C. and 200° C., and, if appropriate,
   (b) in the event that, in formula (I), A represents ethane-1,2-diyl or ethene-1,2-diyl and Ar, R$^1$ and R$^2$ have the abovementioned meaning, the compounds obtained by the process step described under (a), of the general formula (Ia)

in which
Ar, R$^1$ and R$^2$ have the abovementioned meaning, are reacted with a hydrogenating agent, if appropriate in the presence of a catalyst and if appropriate in the presence of a diluent, at temperatures between 0° C. and 150° C.

2. A process for the preparation of (hetero)aralk(en-/in)ylamines of the general formula (I) according to claim 1, in which
   A represents ethane-1,2-diyl (ethylene, dimethylene, —CH$_2$—CH$_2$—) or represents ethene-1,2-diyl (ethenylene, vinylene, —CH=CH—) or represents ethine-1,2-diyl (ethinylene, —C≡C—),
   Ar represents in each case optionally substituted aryl or heteroaryl, each of which has up to 10 carbon atoms and where appropriate 1 to 3 nitrogen atoms and/or one oxygen or sulphur atom as hetero atom(s), the following being selected as preferred substituents: halogen, cyano, nitro, in each case straight-chain or branched alkyl, alkoxy, alkylthio or dialkylamino, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 8 carbon atoms in the individual alkyl moieties, cycloalkyl having 3 to 7 carbon atoms, divalent alkanediyl having 3 to 5 carbon atoms, or alkylenedioxy which has 1 or 2 carbon atoms and which is optionally monosubstituted to tetrasubstituted by fluorine and/or chlorine, or aryl, aralkyl, aryloxy, aryloxyalkyl or aralkoxy, each of which has 6 to 10 carbon atoms in the aryl moiety and where appropriate 1 to 4 carbon atoms in the straight-chain or branched alkyl moiety and each of which is optionally monosubstituted or polysubstituted in the aryl moiety by identical or different substituents from the series comprising halogen, alkyl, alkoxy, alkylthio, halogenoalkyl, halogenoalkoxy or halogenoalkylthio, each of which has 1 to 4 carbon atoms and where appropriate 1 to 9 identical or different halogen atoms, or represents heteroarylalkyl or heteroaryl, each of which has 2 to 9 carbon atoms and 1 to 4 identical or different hetero atoms—in particular nitrogen, oxygen and/or sulphur in the heteroaryl moiety and where appropriate 1 to 4 carbon atoms in the straight-chain or branched alkyl moiety and each of which is optionally monosubstituted or polysubstituted in the heteroaryl moiety by identical or different substituents from the series comprising halogen, alkyl, alkoxy, alkylthio, halogenoalkyl, halogenoalkoxy or halogenoalkylthio, each of which has 1 to 4 carbon atoms and where appropriate 1 to 9 identical or different halogen atoms; and
   R$^1$ and R$^2$ are identical or different and individually represent hydrogen or straight-chain or branched alkyl having 1 to 6 carbon atoms, or together represent alkanediyl (alkylene) having 2 to 6 carbon atoms.

3. A process for the preparation of (hetero) aralk(en-/in)ylamines of the general formula (I) according to claim 1, in which A represents ethane-1,2-diyl (ethylene, dimethylene, —CH$_2$—CH$_2$—) or represents ethene-1,2-diyl (ethenylene, vinylene, —CH=CH—) or represents ethine-1,2-diyl (ethinylene, —C≡C—), Ar represents phenyl, naphthyl, pyridyl, pyrimidyl, triazinyl, furyl, (iso)oxazolyl, oxadiazolyl, thienyl, (iso)thiazolyl or thiadiazolyl, each of which is optionally monosubstituted to trisubstituted, the following being selected as particularly preferred substituents:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, dimethylamino, difluoromethyl, trifluoromethyl, difluoromethoxy, trifluoromethoxy, difluoromethylthio, trifluoromethylthio, methoxycarbonyl, ethoxycarbonyl, n- or i-propoxycarbonyl, methoximinomethyl, ethoximinomethyl, methoximinoethyl, ethoximinoethyl, cyclohexyl, or represents phenyl, benzyl, phenoxy, phenoxymethyl or benzyloxy, each of which is optionally monosubstituted to trisubstituted in the phenyl moiety by identical or different substituents selected from the series comprising fluorine, chlorine, bromine, methyl, ethyl, methoxy, ethoxy, methylthio, trifluoromethyl, difluoromethoxy, trifluoromethoxy and/or trifluoromethylthio, R$^1$ represents hydrogen, methyl, ethyl or n- or i-propyl, and R$^2$ represents methyl, ethyl, n- or i-propyl or n-i-butyl, or together with R$^1$ represents ethane-1,2-diyl (dimethylene), propane-1,3-diyl (trimethylene), butane-1,4-diyl (tetramethylene) or pentane-1,5-diyl (pentamethylene).

4. A process for the preparation of (hetero)arylalk-(en/in)-ylamines according to claims 1 to 3, characterised in that process (b) according to the invention is carried out in the presence of a catalyst.

5. A process for the preparation of (hetero)arylalk-(en/in)-ylamines according to claims 1 to 3, characterised in that the process according to the invention is carried out in the presence of further reaction auxiliaries.

6. A process for the preparation of (hetero)arylalk-(en/in)-ylamines according to claims 1 to 3, characterised in that the process according to the invention is carried out in the presence of a diluent.

7. A process according to claims 1 to 3, characterised in that process (b) according to the invention is carried out under atmospheric pressure or increased pressure up to approximately 200 bar.

* * * * *